United States Patent [19]

Tikijian

[11] Patent Number: 5,608,384
[45] Date of Patent: Mar. 4, 1997

[54] METHOD AND APPARATUS FOR MONITORING FOR THE PRESENCE OF A GAS

[75] Inventor: George H. Tikijian, Zionsville, Ind.

[73] Assignee: SenTech Corporation, Indianapolis, Ind.

[21] Appl. No.: 965,442

[22] Filed: Oct. 23, 1992

[51] Int. Cl.[6] .................................................. G08B 17/10
[52] U.S. Cl. ........................... 340/632; 324/464; 324/468
[58] Field of Search ........................... 340/632; 324/468, 324/464, 470, 438, 459; 250/382, 388

[56] References Cited

U.S. PATENT DOCUMENTS

| | | | |
|---|---|---|---|
| 3,275,883 | 9/1966 | Watters | 315/106 |
| 3,912,967 | 10/1975 | Longenecker | 315/107 |
| 4,297,689 | 10/1981 | Shaw et al. | 340/632 |
| 4,358,683 | 11/1982 | Seifert | 378/101 |
| 4,390,869 | 6/1983 | Christen et al. | 340/632 |
| 4,638,304 | 1/1987 | Kimura et al. | 340/500 |
| 4,816,986 | 3/1989 | Spiridonov et al. | 363/132 |
| 4,910,463 | 3/1990 | Williams, II et al. | 324/468 |
| 4,939,330 | 7/1990 | Berggren et al. | 219/716 |
| 5,010,275 | 4/1991 | van der Wilk | 315/106 |
| 5,198,774 | 3/1993 | Williams, II et al. | 324/468 |

Primary Examiner—John K. Peng
Assistant Examiner—Edward Lefkowitz
Attorney, Agent, or Firm—R. Lewis Gable, Esq.

[57] ABSTRACT

There is a method and disclosed apparatus for detecting for the presence within a gaseous atmosphere of a gas of a concentration above a preset level. The detecting apparatus comprises a sensor including a heater/anode element and a collector/cathode element disposed to define a space therebetween through which the gaseous atmosphere flows. An actuable power supply is coupled to the heater/anode element and to the collector/cathode element for applying power thereto, whereby ionization of the gas causes a current flow through the collector/cathode element of a magnitude proportional to the concentration level of the gas in the gaseous atmosphere. An actuable alarm means provides an indication of the presence of the gas above the preset level. Detecting apparatus control operates the detecting apparatus in a monitoring mode, wherein the power supply is actuated and the alarm deactuated to detect and compare the current flow with the preset level. Upon first detecting current which is equal to or exceeds the preset level, the control operates the detecting apparatus in a leak wait mode, wherein the power supply is actuated and the alarm deactuated to initiate the timing of a period while comparing throughout the period detected current flow with the preset level. If the detected current flow remains equal to or greater than the preset level until the period times out, the control operates the detecting apparatus in an alarm mode, wherein the power supply is deactuated and the alarm is actuated.

20 Claims, 10 Drawing Sheets

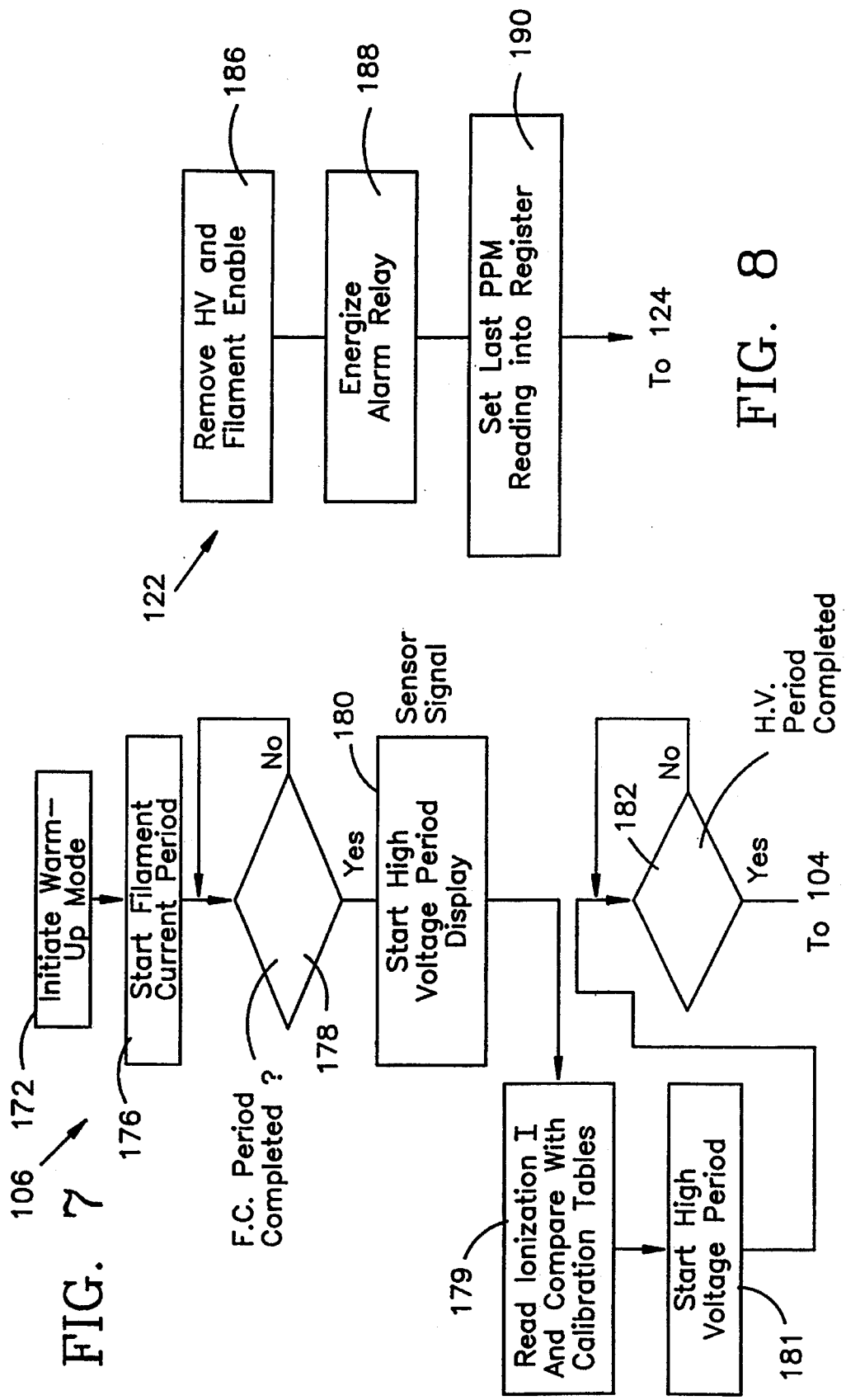

METHOD AND APPARATUS FOR MONITORING FOR THE PRESENCE OF A GAS

FIELD OF THE INVENTION

This invention relates to apparatus and methods for monitoring over an extended period of time for the presence or the leakage of a gas into an enclosure.

BACKGROUND OF THE INVENTION

Sensors are known which take the form of an electrical discharge device for receiving a sample of an atmosphere suspected of containing a concentration of a gas to be detected and comprising cathode and anode elements for producing and collecting ions. The collected ions produce from one of these electrodes a current which varies with the concentration of the gas to be detected. One common use of such electrical discharge devices is as sensors within halogen leak detectors to detect the leakage of halogens and their gas compounds.

Many prior art halogen leak, ion detectors are portable and are carried by an operator to particular site by an operator where a leak of a relatively high level of concentration of halogens is suspected to be present. The operator turns on the leak detector to initiate the detection process. If a gas or halogen leak is detected, the operator typically deactivates the leak detector and proceeds to determine the source of the leak. Halogens are commonly used as refrigerants in domestic and relatively large, commercial refrigeration systems. The leakage of halogen refrigerants has been recognized as a danger to the environment and, in particular, to the depletion of the ozone layer. Taxes have been imposed on the sale of such halogen refrigerant gas, thus giving a financial incentive to closely monitor and prevent the loss of expensive halogen gases.

The halogen sensors in the form of such an electrical discharge device are relatively expensive. The life of such sensors is relatively limited requiring frequent replacement. Experience with that halogen sensor manufactured by Yokagowa Corp. under model No. 6614K11G1 has shown it to have a life of approximately 1500–1800 hours. The collector/cathode elements of such electrical discharge devices are coated with rare earth metals and tend to deteriorate rapidly during sustained collection of the ion stream, as occurs in the presence of halogen gases. In applications wherein such a halogen sensor and its leak detector are used to monitor halogen leaks within a given enclosure such as a refrigeration systems for relatively long periods of time, a halogen leak may occur and is accordingly sensed by the halogen sensor for a relatively long period of time until an operator may intervene to re-set, re-zero or otherwise disable the halogen sensor. During such delay before resetting, the collector/cathode element of the sensor is continually bombarded by the increasing level of ions due to the presence of the halogen. Such extended use quickens the deterioration of the collector/cathode elements and therefore the life of such halogen sensors.

U.S. Pat. No. 4,910,463 of Williams et. al, assigned to the assignee of this invention, disclose a halogen monitoring apparatus capable of monitoring for the presence or leakage of a gas and in particular, halogen, within a given enclosure such as a large commercial refrigeration system. This monitoring apparatus permits extended monitoring of halogen leaks and overcame the problem of the destruction of ion gas detectors by sensing for an increase in the output of the gas sensor and after a fixed, leak wait period deactuating the gas sensor. This gas monitoring apparatus employ illustratively that halogen sensor, which is manufactured by Yokagowa Corporation and described above. The ion stream drawn to its collector/cathode element provide a current of a magnitude proportional to the concentration level of the detected halogen. In particular, this halogen monitoring apparatus senses an increase in the collector/cathode current of a given magnitude and, after a fixed period, reduces the voltage applied between the heater/anode element and the cathode/collector to extinguish the current flow therebetween. Thus such a halogen sensor could be repeatedly used to detect the presence or leakage of a halogen gas, without destroying its collector/cathode element and the resultant shortening of the life of such halogen sensors. Also upon sensing of a cathode/collector current, this halogen monitoring apparatus would provide an alarm to prompt an operator to find and stop the halogen leak.

The Williams et al. Patent '463 avoids issuing false alarms due to the transient presence of the halogens to be detected. If a halogen is present only for a brief time, it is not desired to actuate an alarm, which would bring an operator to fix a gas leak. Williams et al. teaches that a fixed leak wait period is timed out before actuating the alarm. A completed leak wait period of Williams et al. includes three cycles; during each cycle, the gas sensor is deactuated for a first fixed period, before starting a second warm-up period. After the warm-up period, the halogen sensor is again turned on, and if a halogen concentration is detected above the predetermined limit, a second cycle of the wait period commences. William et al. suggest that 3 leak detections be counted, before issuing a valid leak alarm. The total time required for the 3 cycles to run is fixed, before a valid alarm leak is actuated. Further, if the concentration level of the gas detected falls below the set point, the timing process is restarted from the beginning. This has the disadvantage where the gas being monitored is of a concentration level substantially equal to the set point. In those situations, the process of timing 3 cycles may be repeatedly initiated when the sensed level of gas concentration momentarily falls below the set point, thus restarting the recycle process any number of times and thus delaying the actuation of the alarm. Further, the use of a fixed leak wait period does not adequately protect the gas sensor when relatively large concentrations of the halogen detector are detected. Higher ion currents drawn to the collector/cathode element tend to more quickly destroy that element.

U.S. Pat. No. 4,297,689 of Shaw et al. is illustratively of those gas measuring devices, which sense a gas concentration level above a threshold value to actuate an alarm after a variable wait period inversely dependent upon the concentration of the detected gas. However, such gas detecting apparatus do not teach that the sensors are ion-type gas detectors or that the detector is deactuated after a variable period to prolong its life.

Further, the Williams et al. patent '463 describes a circuit for energizing and regulating the temperature of a heater/anode element of its gas sensor, which is more fully described in U.S. Pat. No. 3,912,967 of Longenecker. Longenecker senses the resistance of the heater/anode element and closes a transistor switch coupled to the heater/anode element, when the heater/anode resistance is below a threshold value and opens the switch when the heater/anode resistance exceeds that value. It is important to regulate the temperature of the gas sensor because a change in the temperature results in a change of the background current level, which may be erroneously attributed to the presence of halogen gas. Longenecker provides a coarse control of his heater/anode element temperature by comparing the element's resistance and therefore its temperature to a desired resistance. If less, the transistor switch is disposed from its non-conductive to its conductive state thereby causing an increased current flow through its heater/anode element. The increased current causes the resistance and therefore the temperature of the heater/anode element to rise until it is equal to the desired temperature. When equal, the transistor switch is rendered non-conductive, whereby the current to the heater/anode is reduced. The Longenecker controls the transistor and thus the heater/anode element temperature in an on/off fashion, whereby an increased or decreased current is applied thereto. Longenecker does not teach a proportional control as would provide a finer, more accurate control of the heater/anode temperature.

SUMMARY OF THE INVENTION

It is an object of this invention to provide a new and improved apparatus and method for detecting gas concentration levels substantially equal to the predetermined value to which they are compared and in response thereto actuating an alarm without unduly reinitiating a wait period to eliminate false gas leak alarms.

It is a still further object of this invention to provide a new and improved apparatus and method for protecting the ion collector element of a gas detector when relatively large amplitudes of ion current are detected and for thereby extending the life of the gas sensor.

It is a still further object of this invention to provide a new and improved apparatus and method for measuring the difference between the variable impedance of a heater element of a gas sensor with a reference value and to use that difference to proportionally control the current supplied to the heater element, whereby the stability and accuracy of that gas sensor are improved.

In accordance with these and other objects of the invention, there is disclosed apparatus for detecting the presence within a gaseous atmosphere of a gas concentration above a preset level. The detecting apparatus comprises a sensor including a heater/anode element and a collector/cathode element disposed to define a space therebetween through which said gaseous atmosphere flows. An actuable power supply is coupled to the heater/anode element and to the collector/cathode element for applying power thereto, whereby ionization of the gas causes a current flow through the collector/cathode element of a magnitude proportional to the concentration level of the gas in the gaseous atmosphere. An actuable alarm means provides an indication of the presence of the gas above the preset level. Detecting apparatus control operates the detecting apparatus in a monitoring mode, whereby the power supply is actuated and the alarm deactuated to detect and compare the current flow with the preset level. Upon first detecting a current flow in the collector cathode element which is equal to or exceeds the preset level, the control operates the detecting apparatus in a leak wait mode, wherein the power supply is actuated and the alarm deactuated to initiate the timing of a period while comparing throughout the period the detected current flow with the preset level. If the detected current flow remains equal to or greater than the preset level until the period times out, the control operates the detecting apparatus in an alarm mode, wherein said power supply means is deactuated and the alarm is actuated.

In a further aspect of this invention, the detecting apparatus operates the monitoring apparatus in a leak wait mode to initiate the timing of a period of variable length and, upon termination of the variable period, operates the monitoring apparatus in its alarm mode.

In a further aspect of this invention, a current control circuit is coupled to the heater/anode element for comparing its variable impedance with the reference value to provide an error signal of a magnitude proportional to the difference between the variable impedance and the reference value. The current control circuit is responsive to the error signal for proportionately controlling the amplitude of the current supplied to the heater/anode element, whereby the temperature stability and accuracy of the gas sensor are improved.

BRIEF DESCRIPTION OF THE DRAWINGS

These and other objects and advantages of the present invention will become apparent by referring to the following detailed description and the accompanying drawings, in which:

FIG. 7 shows details of the warm up mode.

FIG. 8 shows details of the steps of the alarm subroutine.

DESCRIPTION OF THE PREFERRED EMBODIMENT

Figure 1:
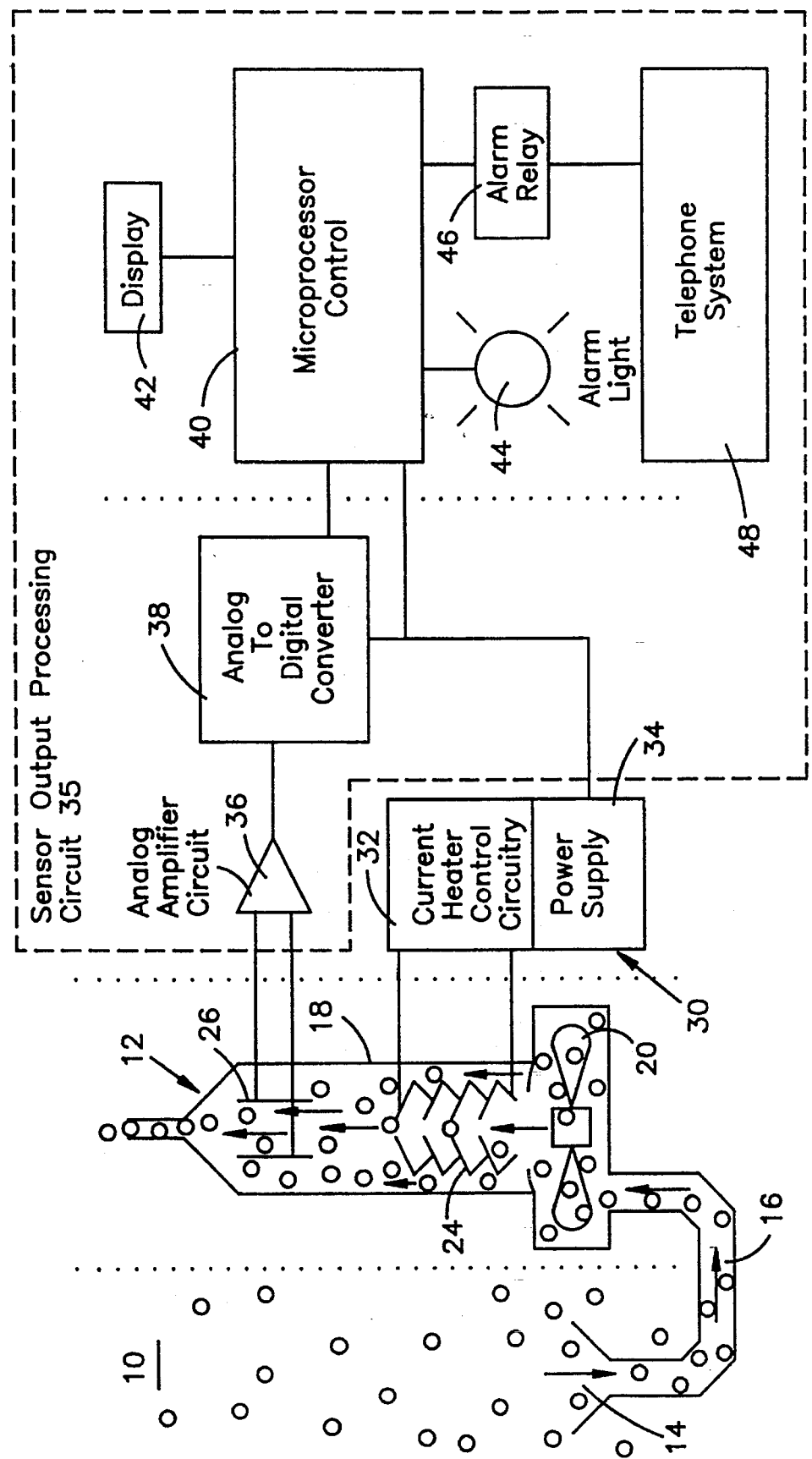
FIG. 1 is a high level, diagrammatic drawing of a gas monitoring apparatus in accordance with the teachings of this invention.

With reference to the drawings and in particular to FIG. 1, there is shown a gas monitoring apparatus 10, which is particularly adapted to monitor the atmosphere within an enclosure to detect the presence of a gas or a family of gases, e.g. halogen, in accordance with the teachings of this invention. The gas monitoring apparatus 10 of this invention includes a gas sensor 12 coupled by a conduit to receive the atmosphere in which the gas to be detected may or may not be present. The atmosphere is drawn through an intake 14, the conduit 16 and into an ionization chamber 18 by a fan 20. The sensor 12 is adapted in an illustrative embodiment of this invention to sense halogens and, to that end, is adapted to heat the sample of the atmosphere drawn into its ionization chamber 18, to a temperature of approximately 900° C. Heating the sample atmosphere to such a temperature ionizes any halogen based hydrocarbons present in the sample. A relatively negative voltage is established upon a collector/ cathode element 26 of the sensor 12, thus attracting any positively charged halogen ions thereto and establishing a small current ion flow, which is applied, as shown in FIG. 1, to a sensor input of the processing circuit 35. The amplitude of that ion current is proportional to the relative concentration of the halogen gas in the sampled atmosphere. A sensor power circuit 30 applies a voltage across the heater/anode element 24, which heats the sampled atmosphere to the desired temperature. In an illustrative embodiment of this invention, the gas sensor 12 may take the form of that sensor manufactured by Yokagowa Corp. under its designation 6614K11G1. The collector/cathode element 26 thereof illustratively takes the form of a rod suspended in a powered-alkaline metal core housed in a concentric platinum tube. The tube and rod are connected by a welded platinum strip, thus keeping rod and tube at the same potential. The heater/anode element 26 may illustratively take the form of a coiled/wire or filament wrapped about four carminic posts and dispose about the aforementioned rod/tube assembly. The filament is made of a material, e.g., platinum, whose impedance (resistance) is variably dependent upon its temperature and thus the temperature of the gaseous atmosphere directed thereby. The temperature dependent property of the anode's filament is used as will be described below to control its energization. Illustratively, a voltage in the order of a 180 volts is imposed between the heater/anode element 26 and its collector/cathode element 24. Approximately 4 volts is applied across the heater/anode element 13, whereby current in a normal range of 3.5 to 4 amps is directed therethrough and the temperature of the gas sensor 12 is raised to approximately 900° C., causing the ion current to flow in the rod of the collector/cathode element 26.

The sensor power circuit 30 includes the current heater control circuit 32, which senses the impedance, e.g., resistance, of the filament forming the heater/anode element 24 to thereby sense the element temperature and therefore the temperature of the sampled atmosphere within the ionization chamber 18. As will be explained, that sensed filament resistance is used to control the current, typically in the range of 3.5 to 4 amps, which is applied to the heater/anode element 24, whereby the filament current and therefore its temperature are precisely controlled. The sensor power circuit 30 also includes a power supply 34, which controls the application of the relatively high voltage, e.g., 180 V DC, across the heater/anode element 24 and the collector/cathode element 26 of the gas sensor 12.

The gas monitoring apparatus 10 also comprises, as shown in FIG. 1, the sensor output processing circuit 35, which is coupled to the collector/cathode element 26 to receive and to process the ion current to provide on a display 42 an indication of the concentration of the detected gas. The sensor output processing circuit 35 comprises an analog amplifier circuit 36 for amplifying and applying the ion current to an analog-to-digital converter 38, which converts the analog ion current to a digital word or output, which is a digital representative of the amplitude of the ion current. In turn, that digital word is applied to a microprocessor control 40, which as will be explained in detail below processes that digital word to provide upon the display 42 an indication of the gas concentration and to actuate an alarm light 44 and an alarm relay 46, whereby an alarm signal may be transmitted over a conventional telephone system 48 to a remote location. It is contemplated that a plurality of the gas monitoring apparatus 10, as shown in FIG. 1, may be disposed at a plurality of remote locations and that each would be coupled by the telephone system 48 with a centrally located monitoring station, whereby a single operator may monitor the presence or leaking of gas into the enclosures, typically in the form of a commercial refrigerator at the remote locations. For example, a food chain could monitor its produce refrigerators at each store of that chain from a single, centrally located station.

Figure 2A:
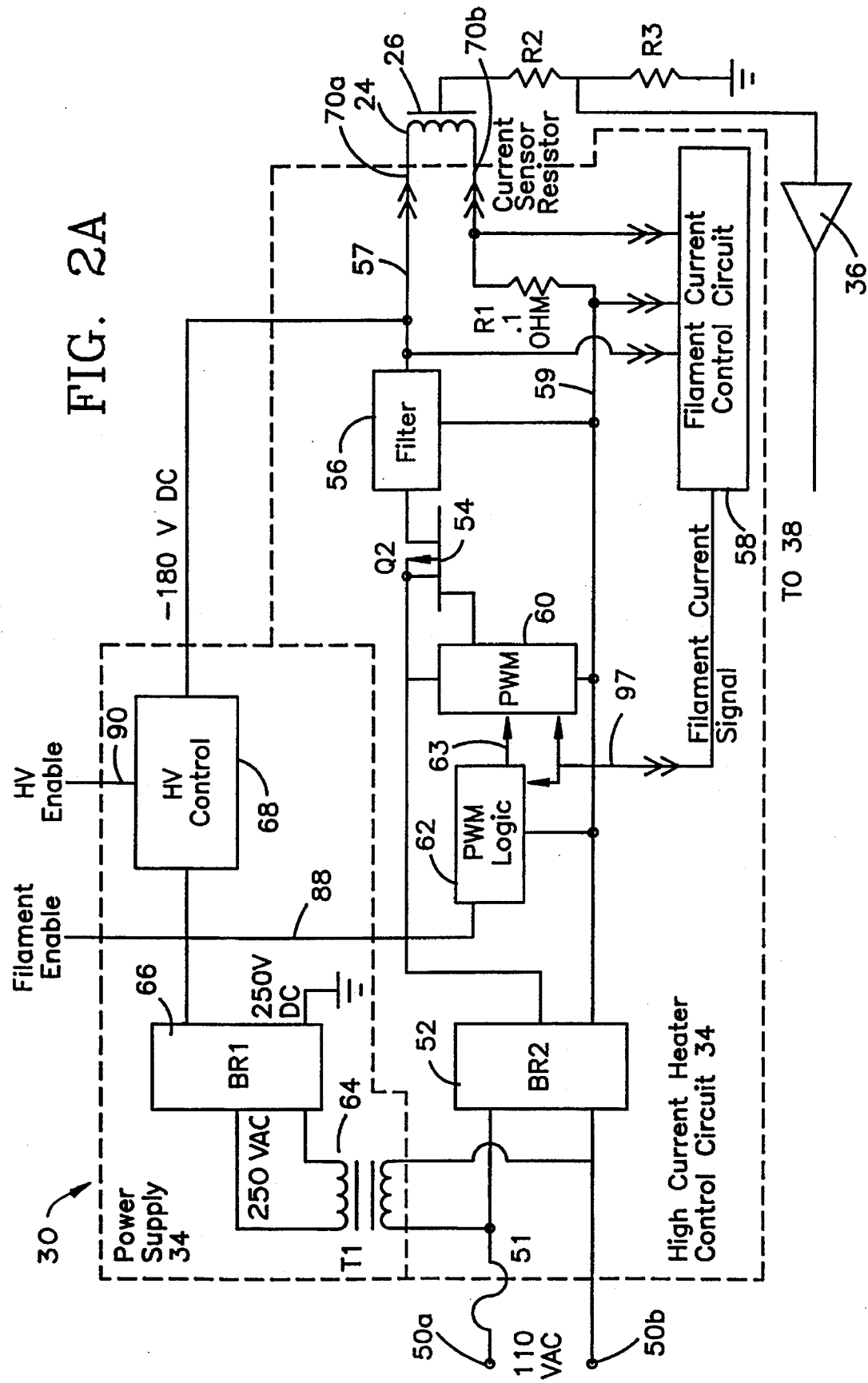
FIG. 2A is a diagrammatic drawing of a sensor power circuit for supplying power to a gas sensor of the gas monitoring apparatus as shown in FIG. 1.
Figures 1, 2B:
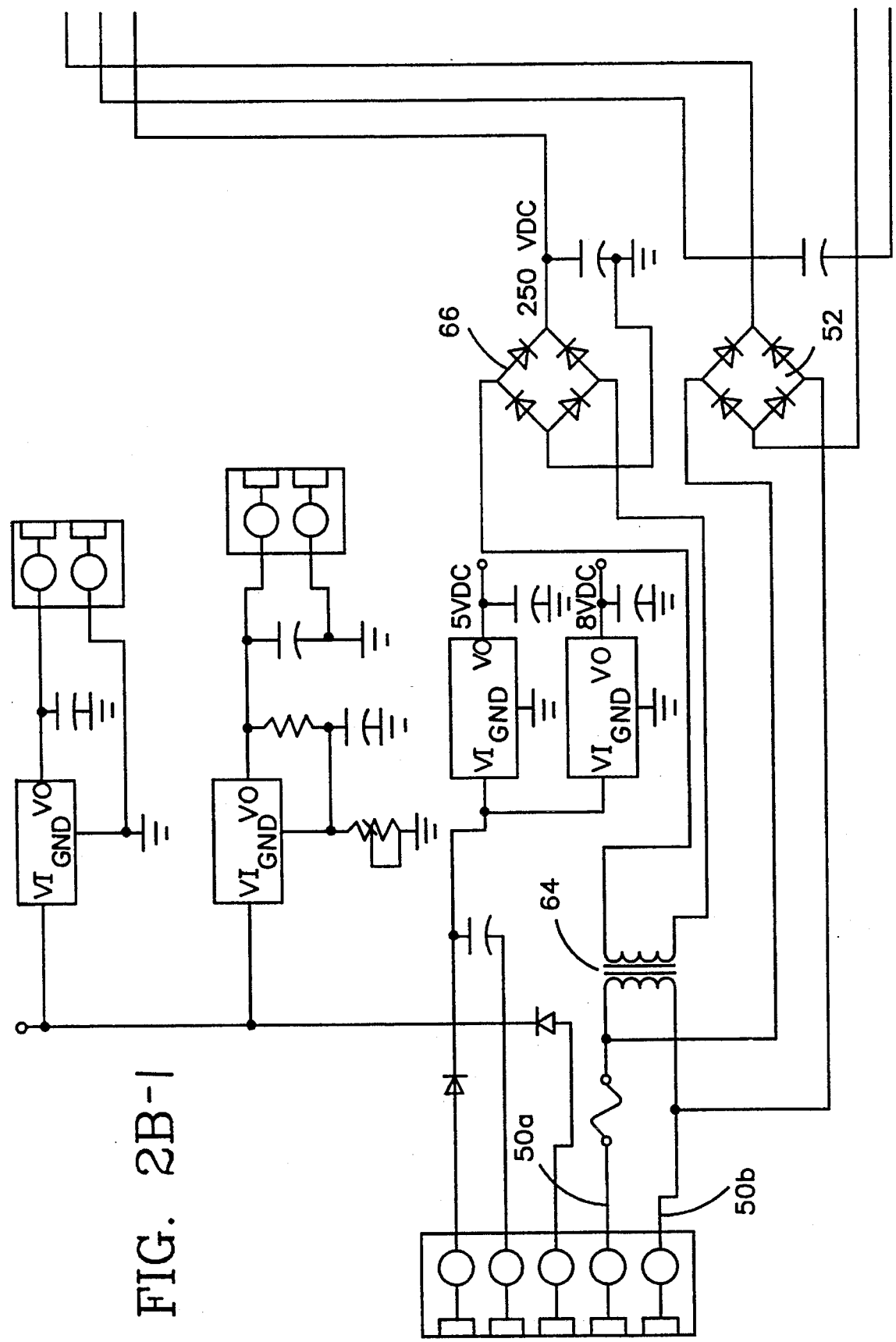
FIG. 2B is detailed schematic drawing of the sensor power circuit.
Figures 2, 2B:
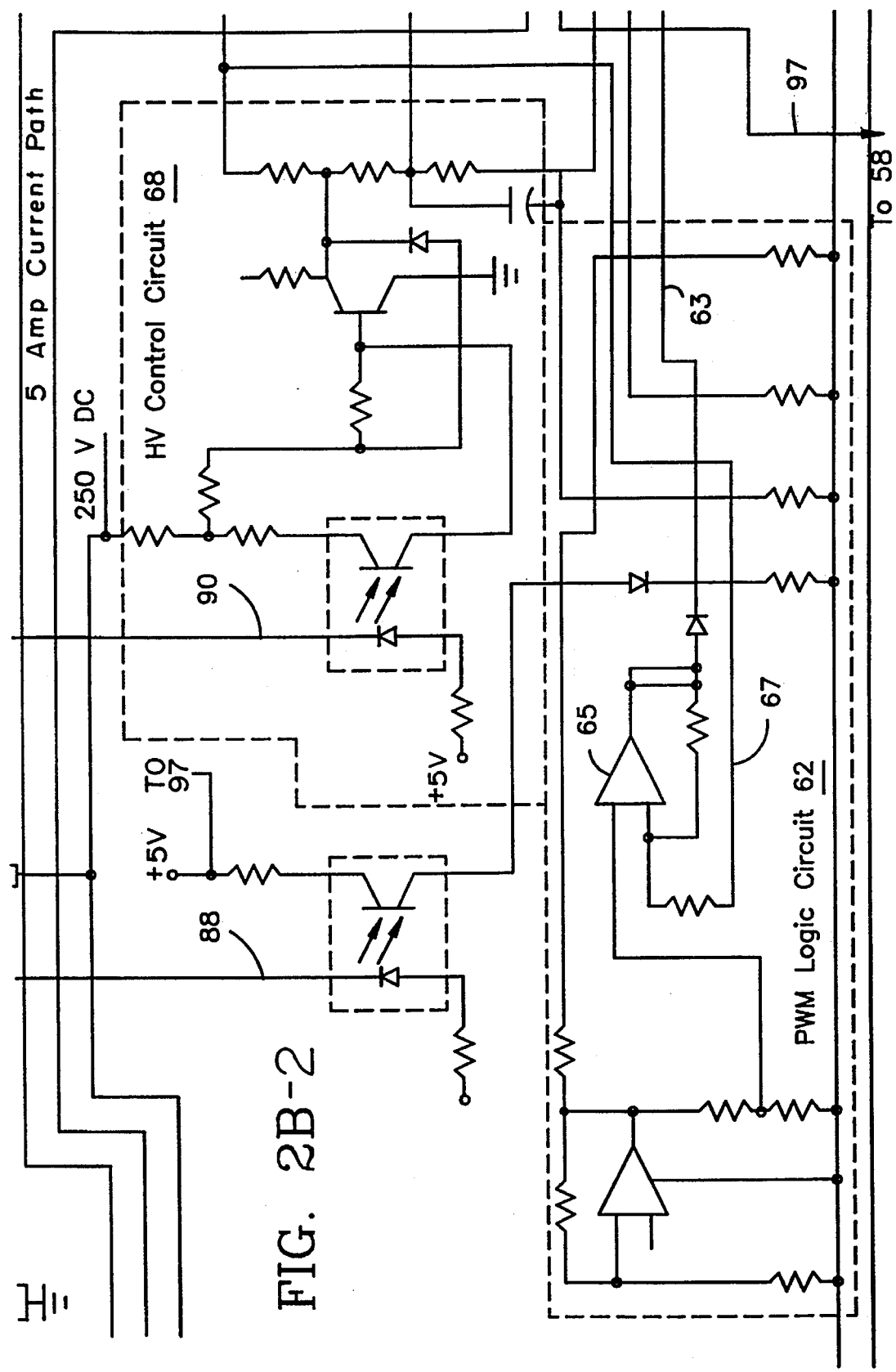

Referring now to FIG. 2, the current heater control circuit 34 comprises a bridge 52 coupled to an input power source, e.g., 10 V AC, via a fuse F1 to provide DC power to the circuit 34. The selective application of the DC output voltage of the bridge 52 is controlled by a power switch in the form of a power transistor 54, which is selectively turned on and off by a pulse width modulator (PWM) 60, whereby a sequence of pulses is outputted from the transistor 54. In turn, these pulses are smoothed by a filter 56 before being applied across the heater/anode element 24 via filament output terminals 70*a* and *b*. The filter 56 "smooths out" or filters the series of pulses, whereby a DC current of selected amplitude is applied through the filament comprising the heater/anode element 24. The current amplitude applied to the heater/anode element 24 is controlled proportionately to the amplitude of the error signal output by a filament current control circuit 58, which is coupled to the heater/anode element 24 to sense its resistance and therefore its temperature. The circuit 58 responds thereto to apply its error signal to the pulse width modulator 60, whereby the power transistor 54 is turned on and off at a controlled pulse width rate, whereby its filtered output is of a controlled current amplitude to maintain the current and therefore the temperature of the element 24 at a precise level. It is appreciated that the temperature of the atmosphere to be monitored may vary and that consequently the sampled atmosphere drawn into the ionization chamber 18 may likewise change. This invention appreciates that changes of atmosphere temperature, as well as the rate of the atmosphere flow through the ionization chamber 18, effect the temperature of the heater/anode element 24 and that, in turn, the filament temperature changes or drifts may cause corresponding errors in the amplitude of the collected ionization current which are independent of the gas concentration to be detected. This invention recognizes that the filament comprising the heater/anode element 24 is typically a platinum wire, which has the desired characteristic of acting as an accurate temperature sensor, i.e., its resistance accurately reflects its temperature. Thus, to compensate for changes or drifts in the sampled environment temperature and any fluctuations of the environment flow rate thereof through the ionization chamber 18, the difference between the resistance of the element 24 and a reference value is sensed by the filament current control circuit 58 to thereby proportionately control the amplitude of the current flowing through and therefore the temperature of the element 24. This proportionate control of the amplitude of the current applied to the heater anode element 24 achieves a closer, more accurate control of the heater/anode element temperature than achieved by increasing the element current by a fixed amount. Thus, the amplitude of the output signal from the sensor 12 is a more accurate indication of the concentration level of the detected gas.

Further, the current heater control circuit 34 includes a pulse width modulation (PWM) logic circuit 62, which is responsive to an enable signal applied via a filament enable line 88 from the microprocessor control 40, to selectively turn on and off the power transistor 54, whereby the relatively high levels of current may be removed from the filament comprising heater/anode element 24. As will be described below, upon sensing the presence of a gas and in particular a halogen gas, the gas sensor 12 is deactivated, whereby the flow of halogen ions to the collector/cathode element 26 is stopped and the life of the gas sensor 12 prolonged.

Further, the PWM logic circuit 62 provides a current limiting signal via line 63 to the pulse width modulator 60 to provide protection during the warm-up mode. When the sensor 12 and it's elements 24 and 26 are relatively cool, the current applied to the filament of the heater/anode element 24 is limited to a maximum amplitude, e.g., 5 amps. Once the sensor 12 and it's element 24 and 25 have warmed up, the logic circuit 62 permits the current applied to the element 24 to be set in the normal range, e.g., 3.5 to 4 amps. In the warm-up mode, the collector/cathode element 26 is relatively cold and its resistance relatively low. Thus, if the current supply to the heater/anode element 24 were not appropriately controlled by the pulse width modulator 60, the current drawn from the collector/cathode element 26 may surge quickly to a magnitude, which would destroy the elements of the gas monitoring apparatus 10 and, in particular, the power transistor 52.

FIG. 2B illustrates in detail the circuit diagram of the high current heater control circuit 34 with like elements being identified by the same numerals and how the PWM logic circuit 62 applies its control signals via line 63 to limit the current output signal developed by the pulse width modulator 60. As will be explained below, the filament control current circuit 58 applies during the warm-up mode a boot strap signal to the pulse width modulator 60, whereby a relatively fixed current, e.g., 5 amps, is applied to the heater/anode element 24, thus causing it to rapidly heat. A feedback line 67 applies a signal proportional to the current flowing through heater/anode element 24 to the PWM logic circuit 62 and in particular to the plus terminal of an operational amplifier 65. A reference voltage is applied to the other, negative terminal of the operational amplifier 65, thus limiting its output as applied via line 63 to the SD input of the pulse width modulator 60, whereby its output is limited such that the warm-up current flowing to the heater/anode element 24 is limited.

Figures 2, 2B, 3:
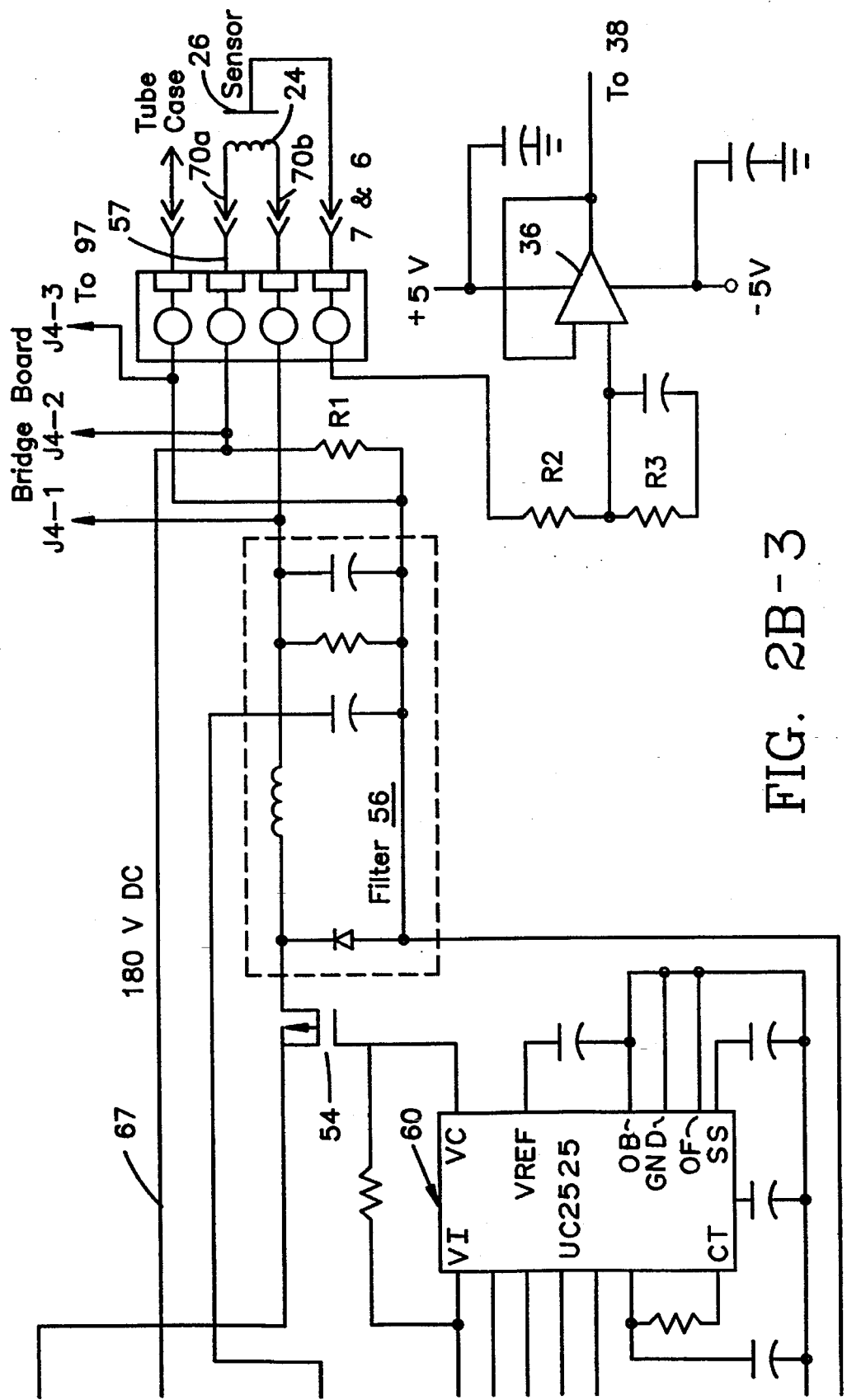
FIG. 3 is a sensor output processing circuit for receiving and processing the output of the gas sensor of the gas monitoring apparatus as shown in FIG. 1.
Figure 3:
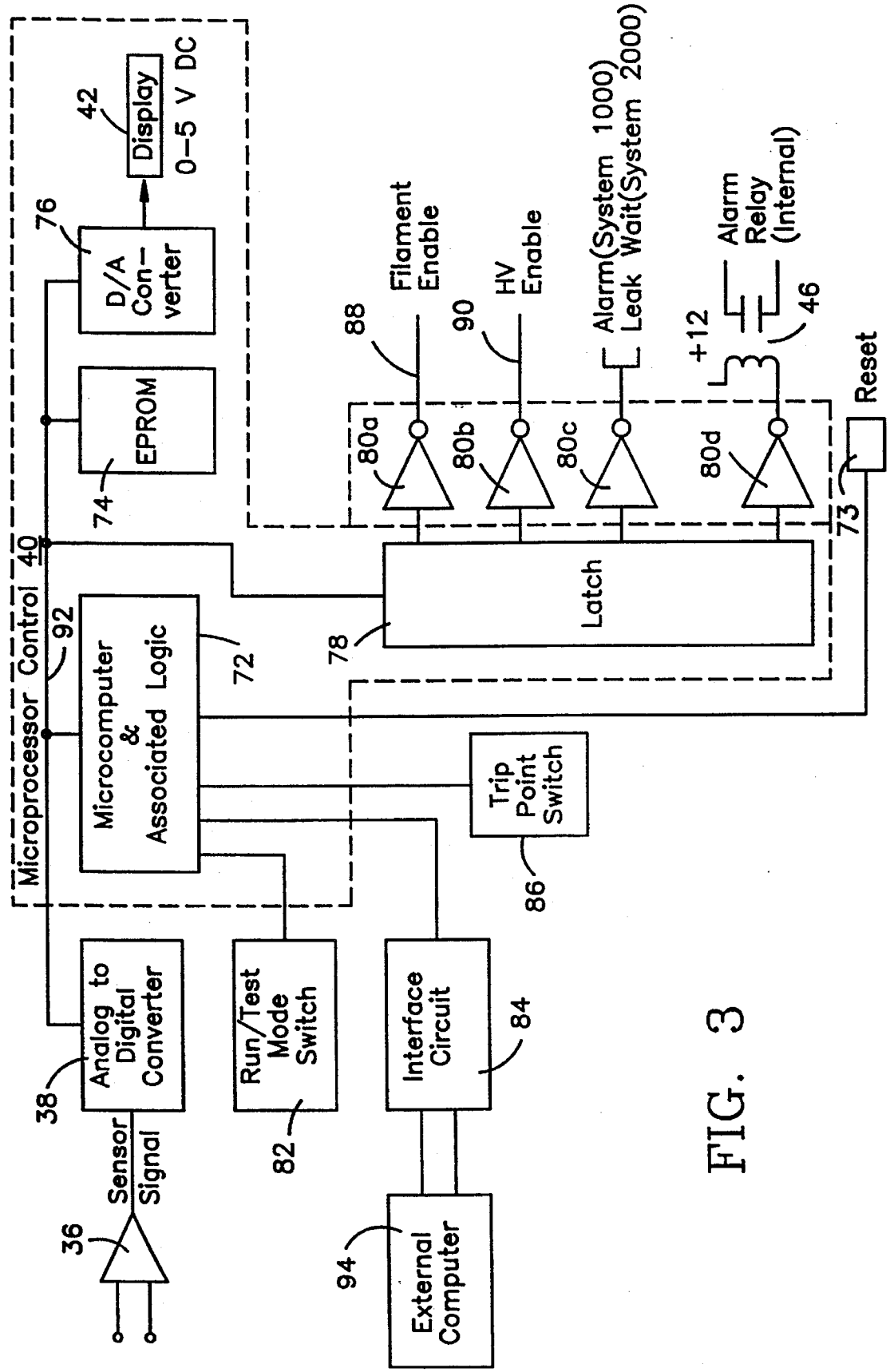

After the warm-up mode has expired, the microcomputer 72 causes the latch 78 and the operating driver 80b to apply an enable signal via the high voltage enable line 90 to the high voltage control circuits 68, which is closed thereby to permit a high voltage to be applied across the heater/anode element 24 and the collector/cathode element 26. As a result, a signal current is drawn from the element 26 through the voltage divider network comprised of resistors R2 and R3. The voltage across resister R3 is buffered by the analog amplifier 36, which is a unity gain amplifier, before being applied via the analog-to-digital converter 38 to a microcomputer 72, as shown in FIG. 3. When the sensor 12 is relatively cool, the resistance of the filament comprising the element 24 is relatively low, so that current is limited to a maximum of 5 amps as described above. After the warm-up period, the sensor 12 is operated so that current applied to the heater/anode element 24 lies in a normal range, e.g., 3.5 to 4 amps. The sensor output drawn from the collector/cathode element 24 varies in a range from 0.1 volts or less when no gas is detected to a high of 1.5 volts at 100 PPM, when the system is calibrated in its calibration mode for 100 PPM full scale; the calibration mode will be described below.

The sensor power circuit 30 comprises a transformer 64, whose primary winding is coupled via the fuse F1 to the voltage input terminal 50a and to terminal 50b, whereby the relatively low alternating voltage, e.g., 10 V AC, is increased to a relatively high level, e.g., 250 V AC. The relatively high voltage is applied to a second bridge 66 to output therefrom a DC voltage. The application of that DC voltage is controlled by a high voltage control circuit or switch 68, whereby the high voltage may be selectively applied and removed from the sensor 12 and in particular from across its elements 24 and 26. In particular, the microprocessor control 40 applies an enable signal via a high voltage enable line 90 to the control circuit 68 to apply and to remove the high voltage. For example, when the presence of halogen gas has been sensed, the control circuit 68 may be disabled to remove the voltage from across the elements 24 and 26 of the sensor 12.

The microprocessor control 40 shown generally in FIG. 1 is shown in more detail in the block diagram of FIG. 3. In particular, the microprocessor control 40 includes a microcomputer and assorted logic 72, which is coupled via a data/address bus 92 to the analog-to-digital converter 38, whereby the ionization current as amplified by the analog amplifier 36 and converted to a digital word by the converter 38 may be processed by the microcomputer 72, a memory in the form of an microcomputer 72, a digital-to-analog converter 74 whereby the digital signals appearing on the bus 92 may be converted to corresponding analog signals, and a latch 78.

As will be described in detail below, the gas monitoring apparatus 10 is capable of being operated in the following modes: warm-up, monitoring, test, leak-wait, alarm and calibration. The operator may manually set a run/test mode switch 82 in one of its corresponding positions, run or test, to thereby determine in which mode the apparatus 10 is to operate. A trip point set switch 86 is also coupled to the microcomputer 72, whereby the set point in terms of the concentration of the gas to be detected, e.g., PPM of halogen gas, may be set. As will be explained in detail, the microcomputer 72 processes the ionization current derived from the collector/cathode element 26 to determine whether the concentration of the gas within the sensor 12 is above or below the point set by the switch 86. The microcomputer 72 is further coupled to an interface circuit 84, whereby the microcomputer 72 may be coupled to an external computer 94. Typically, the external computer 94 is disposed at the same location as the gas monitoring apparatus 10 and is primarily used to control some other function; the external computer 94 may be used to interrogate the microcomputer 72 as to the measured gas concentration values. The microcomputer 72 sets the latch 78 whereby outputs are developed from selected of a plurality of output drivers 80a, 80b, 80c and 80d. As shown in FIG. 3, the output of the output driver 80a provides an enable signal via the filament enable line 88 to control the PWM logic circuit 62 as shown in FIG. 2. The output driver 80b applies an enable signal via the high voltage enable line 90 to the high voltage control circuit 68 as shown in FIG. 2.

When the gas monitoring apparatus 10 has sensed a gas concentration above the set point and the leak wait mode has timed out, the microcomputer 72 enters the alarm mode. In the alarm mode, the output driver 80c applies an alarm signal internally to actuate for example the alarm light 44, and the output driver 80d closes the alarm relay 46 whereby, as illustrated in FIG. 1, an alarm message may be transmitted via the telephone system 48 to a centralized station. In order to exit the alarm mode, it is necessary to externally reset the gas monitoring apparatus 10. As shown in FIG. 3, an operator may intervene by manually actuating a reset switch 53, whereby the gas monitoring apparatus 10 is disposed from its alarm mode to its monitoring mode. Alternatively, the switch 73 may be a register, which is set from the centrally disposed station over conventional telephone lines. In this fashion, the gas monitoring apparatus 10 will continue in its alarm mode until the leak within the environment is found and repaired, and external intervention occurs in the form of throwing the reset switch 73.

Figure 4:
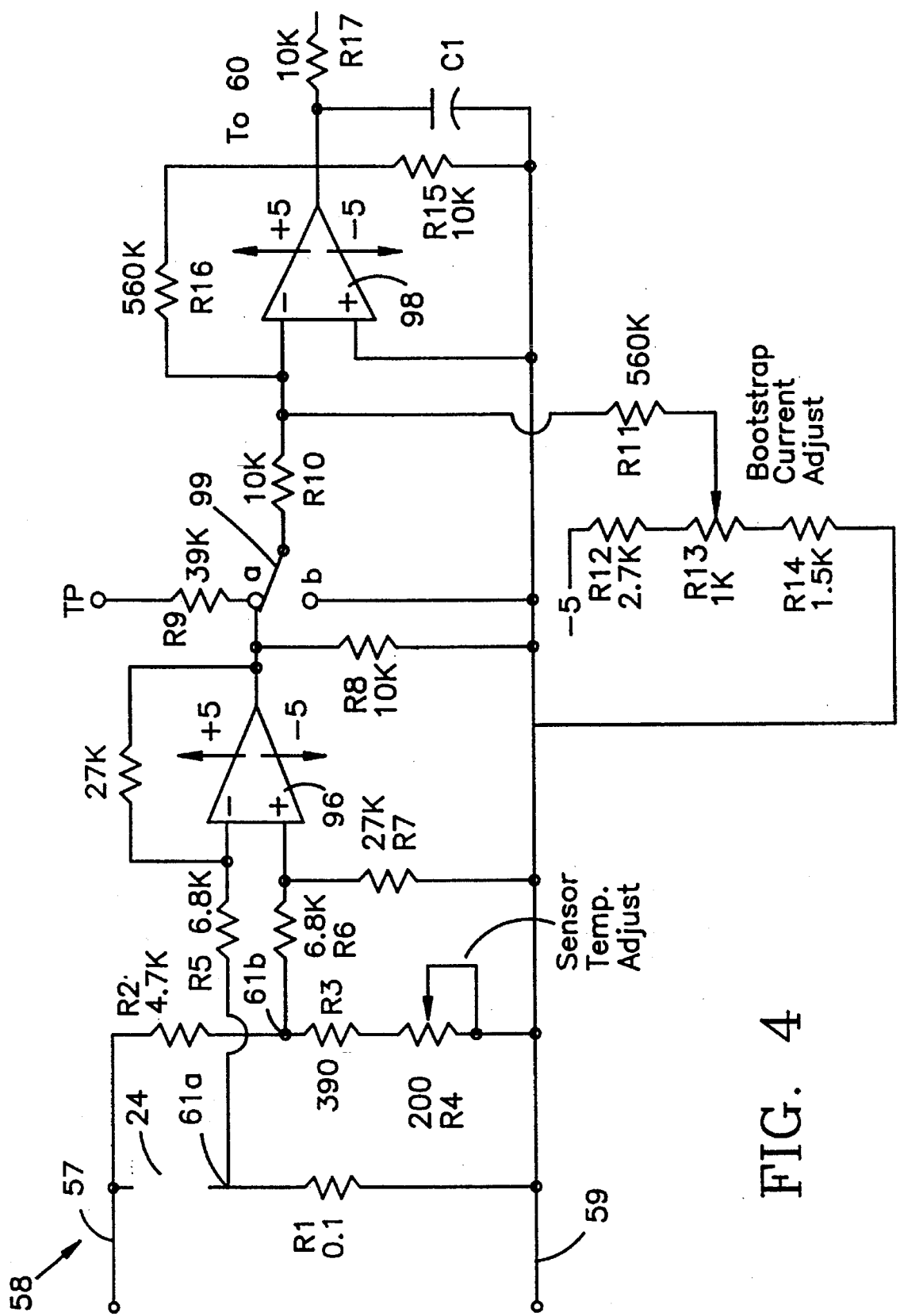
FIG. 4 is a detailed schematic drawing of a filament current control circuit, which is responsive to the variable impedance of a heater/anode element of the gas sensor for in turn controlling the current and therefore the temperature of the heater/anode element.

The filament current control circuit 58 shown generally in FIG. 2 is shown in greater detail as the circuit diagram of FIG. 4. Essentially, the circuit 58 comprises a Wheatstone bridge comprised of a first leg in the form of the filament making up the heater/anode element 24, a second leg in the form of a resister R1 of an illustrative value of 0.1 ohm, a third leg in the form of resister R2 and a fourth leg comprised series connected resister R3 and potentiometer R4. The potentiometer R4, as will be explained, sets the temperature at which the filament of the element 24 is to be controlled. In particular, the filament of the element 24 is made of a temperature sensitive material, e.g., platinum, whose resistant varies accurately as a function of temperature, whereby when the temperature and thus the resistance of the filament comprising the element 24 varies, an error signal is developed across the bridge output taken from terminals 61a and 61b. As shown in FIG. 2, power is supplied to the Wheatstone bridge 24 and the filament current control circuit 58 via lines 57 and 59, which are coupled via the filter 56 to the output of the bridge 52. The Wheatstone bridge output is successively amplified by a pair of operational amplifiers 96 and 98, when a run/calibration mode switch 100 is disposed in it's run position "a". The output of the filament control circuit 58, which is indicative of the difference between the set or desired temperature and the measured temperature, is applied via a control line 97 to the pulse width modulator 60, whereby the pulse width modulation ratio and thus the current applied to the element 24 are controlled to keep the current and therefore the temperature of the filament comprising the heater/anode element 24 at the level set by the sensor temperature potentiometer R4.

The error signal derived from the Wheatstone bridge is summed with a base current derived from a boot strap current potentiometer R13, which is adjusted when the gas monitoring apparatus is disposed in its calibration mode. Typically, each sensor 12 is calibrated at the factory during the calibration mode. In particular, the run/calibration mode switch 99 is disposed to it's position "b" whereby the error signal developed by the Wheatstone bridge is ignored and only the base current is applied to the operational amplifier 98. At the beginning of the warm-up mode, the temperature of the filament comprising the heater/anode element 24 is relatively cold, whereby the output of the filament current control circuit 58 is substantially zero. In order to provide a suitable control voltage to the pulse width modulator 60 to initiate a current flow through the filament of the cathode/heater element 24, the base or boot strap current is developed from the boot strap potentiometer R13 to develop a suitable output from the circuit 58, whereby the pulse width modulator 60 is controlled to turn on the power transistor 54 to initiate a current flow through the heater/anode element 24. The value of the base or boot strap current applied to the operational amplifier 98 is set during the calibration mode to provide an illustratively output from the filament current control circuit 58 in the order of 2.2 volts.

Figure 5:
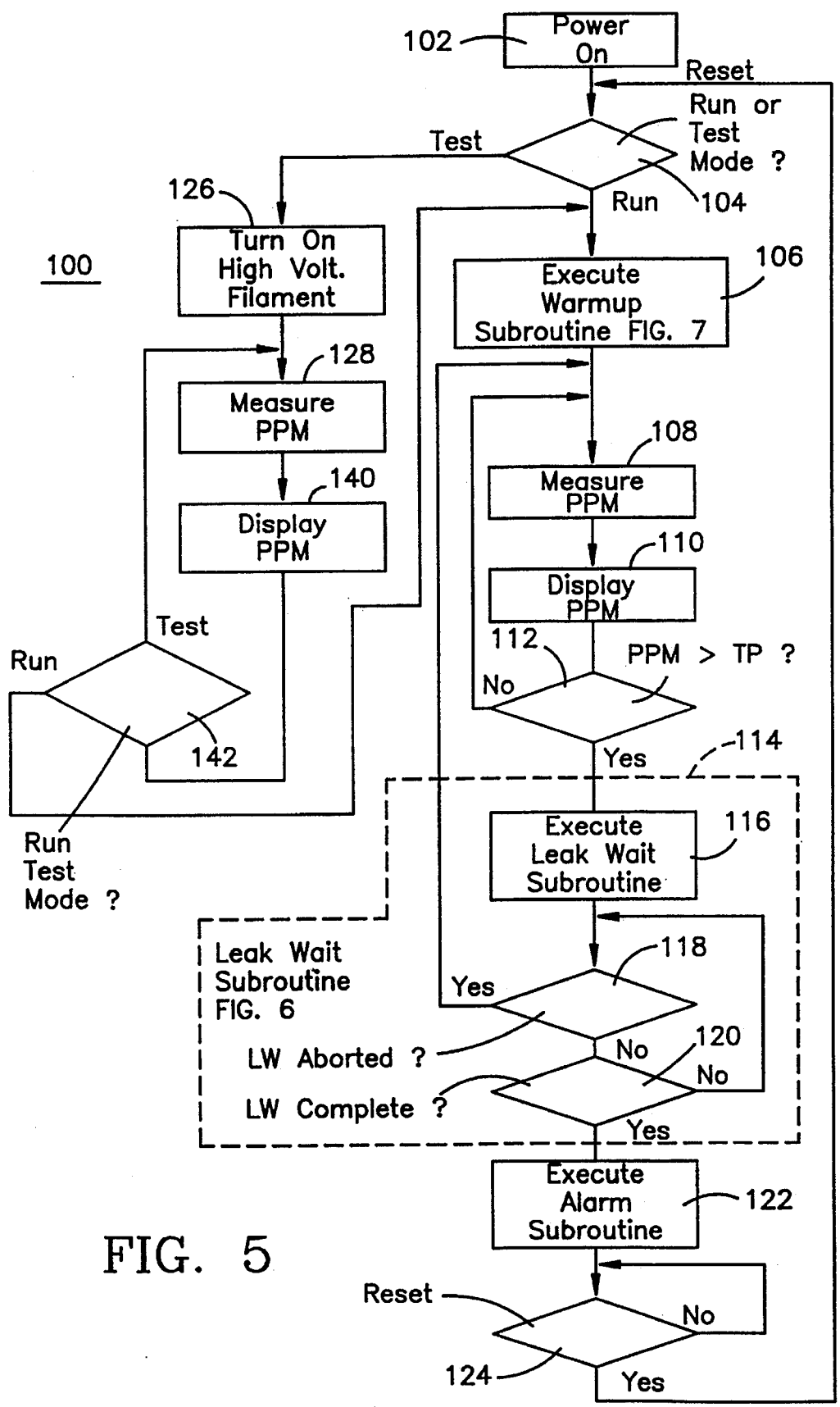
FIG. 5 is a flow diagram of the main program as stored within a memory and executed by a microcomputer as shown in FIG. 3.

The operation of the gas monitoring apparatus 10 is controlled in accordance with a computer program which is represented by the flow diagram shown in FIG. 5 and which is stored in the EPROM 74 as shown in FIG. 3. More specifically, the program 100 controls which mode, i.e., warm-up, monitoring, test, leak-wait, alarm, or calibration, that the gas monitoring apparatus 10 is currently disposed and, further, controls accurately the current and therefore the temperature of the filament comprising the heater/anode element 24, whereby the accuracy of the output of the gas monitoring apparatus 10 in terms of the detected concentration level of gas is significantly improved. In step 102 power is applied. Preferably, power is applied when the gas monitoring apparatus 10 is initially installed by hard wiring the apparatus 10 to the power bus. Since apparatus 10 is a monitoring apparatus, it is preferred that no power-on switch be installed to prevent an operator from turning off the apparatus 10.

Next in the main program 100, step 104 examines in which position the run-test mode switch 82 is disposed, i.e., whether in it's test mode position or monitor mode position. If in it's run or monitor mode position, the main program 100 moves to step 106, thus placing the gas monitoring apparatus 10 in it's warm-up mode and executes the warm-up subroutine shown in greater detail in FIG. 7. In the warm-up mode, a relatively high current is applied for a first predetermined period to the heater/anode element 24 without applying a voltage between heater/anode element 24 and the collector/cathode element 26. After the first period has timed out, the warm-up mode then applies the high voltage between the elements 24 and 26 for a second period, which is set typically shorter than that of the first period to permit any ions generated during the first period to be collected and the resulting transient peaks in the collected ion current to die out before operating in the monitoring mode. In the warm-up mode as shown in FIG. 7, step 172 initiates the warm-up mode by simultaneously actuating the latch 78 and it's output driver 80a to apply a filament enable signal via line 88 to the PWM logic circuit 62, whereby the pulse width modulator and the power transistor Q2 are enabled to apply a relatively high current through the filament of the heater/anode element 24 and to set a count into a first or filament current counter, before step 176 starts counting that first period and decrementing the filament current counter. Step 178 tests whether the filament current period has been completed. After the first or filament current period, e.g., 2.5 minutes, has timed out, step 180 starts a second or high voltage period by actuating the latch 78 and it's output driver 80b to apply a high voltage enable signal via line 90 to the high voltage control 68, whereby a high voltage in the order of 180 V DC is applied across the elements 24 and 26 of the sensor 12, and sets a count within a high voltage period counter. As a result, a current begins to be drawn from the collector/cathode element 26 and is compared with a calibration table stored within the EPROM 74 to develop a digital word which is directly proportional to the PPM level of the read ionization current from the sensor 12. The developed digital word is applied to the digital-to-analog converter 76, which in turn applies an analog signal to display the concentration level of the sensed gas on the display 42. Next, step 181 starts the high voltage period by decrementing the high voltage period counter. Step 182 determines whether the high voltage counter has timed out and when it has timed out, the program returns to step 104 of FIG. 5.

After the gas monitoring apparatus 10 has been warmed up, the main program 100 moves to step 108, which disposes the gas monitoring apparatus 10 in it's monitoring mode and begins to measure the ionization current drawn from the collector/cathode element 26 of the sensor 12. In particular, the sensed analog ionization current is converted by the analog-to-digital converter 38 to a corresponding digital word. Thereafter that digital word is applied to a calibration look up table, whereby a corresponding digital word indicative of the linear value of the concentration level of the sensed gas. Thereafter the linearized digital word is converted by the digital-to-analog converter 76 to a corresponding analog signal to be displayed upon display 42 in step 110. Next in step 112, the same digital word indicative of the measured, linearized value of the ion current, is compared with that set point entered via the trip point switch 86. If the measured ionization current is below the trip point, step 112 returns the program to step 108, whereby the program 100 continues to sequence through steps 108, 110 and 112 and to stay in the monitoring mode until a concentration of the sensed gas equal to or greater than the set point is determined; then the program 100 moves to the leak wait subroutine 114 and the gas monitoring apparatus 10 is disposed in it's leak wait mode.

As generally shown in FIG. 5, the leak wait subroutine 114 moves to step 116 to execute the leak wait subroutine. The purpose of the leak wait mode is to prevent false alarms caused by transient conditions. Basically the leak wait subroutine 114 establishes a first fixed period and, if the sensed concentration level remains above the set point after the first fixed period, a second variable period, whose length is inversely dependent upon the sensed concentration level. If the ionization current falls below the set point during the second variable period, a third fixed period is timed before the apparatus returns to the monitoring mode. It is desired to prevent the random introduction of the gas from actuating the alarm mode. The alarm mode is entered when there is a continuous introduction of the gas to be detected, as would be indicative of a leak of the refrigerant or halogen gas into the refrigerator. An extraneous sample of gas will be quickly removed as the fan 20 drives the atmosphere and the gas through the ionization chamber of the sensor 12. The first period is timed to permit the extraneous sample of the gas to be discharged. If the first fixed period were eliminated, the second period may not last long enough to expel the gas when concentration levels of the gas are relatively large and false alarms might result. If during the first period, further readings of the ionization current fall below the set point, step 112 returns the program 100 to the monitoring mode and in particular to step 108 to continue to measure the gas concentration. If the first period times out, the second period is initiated and if during that period, the measured gas concentration falls below the set point, step 120 terminates the timing of the second variable period and commences timing a third fixed period. If the second period times out as determined by step 120 with the gas concentration level above the set point, the program 100 moves to the alarm mode of the gas monitoring apparatus 10 and executes the alarm subroutine 122. If the sensed concentration level falls below the set point during the third period, the program returns to the monitoring mode. However, if the sensed concentration level exceeds the set point during the third period, the leak wait mode does not restart timing the second variable period but continues directly to time it until completion. In this fashion, the leak wait mode of this invention processes sensed concentration levels substantially equal to the set point without unduly delaying the onset of the alarm mode.

Figure 6:
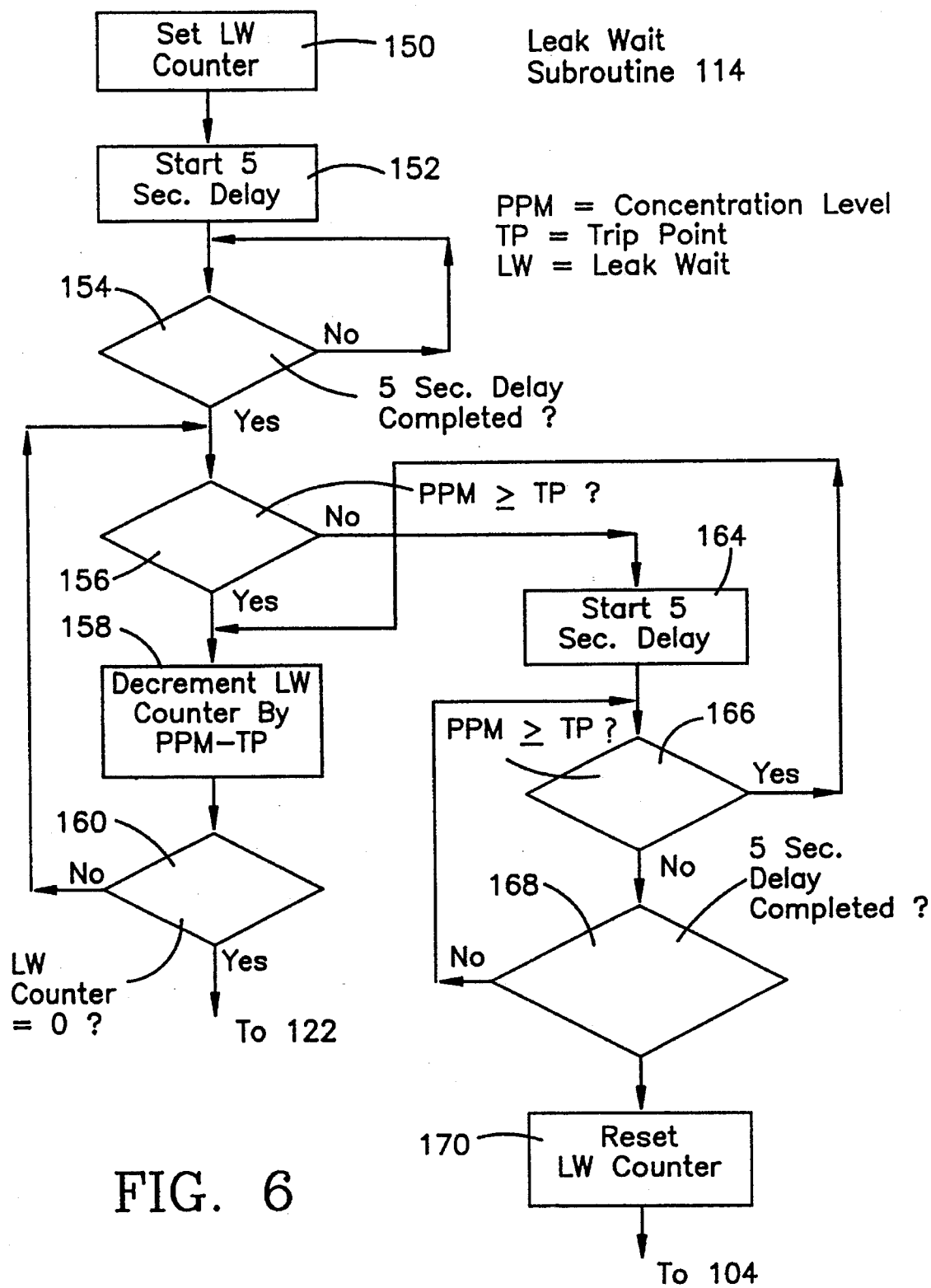
FIG. 6 is a subroutine of the main program executed by the microcomputer for determining a variable leak wait period between the sensing of sensor current above a predetermined said point and the deactuation of the sensor.

FIG. 6 shows the steps of the leak wait subroutine 114 in greater detail. Upon determining that the sensed ionization current is equal to or greater than the set point, the program 100 moves to step 150, which sets a count into a leak wait counter corresponding to the sensor reading calibrated for full scale and not on the digital value of the sensed gas concentration. The leak wait counter, which is formed in the EPROM 74, will be decremented at a fixed rate to time the second variable period as will be explained. Next, step 152 initiates timing of the first fixed period or delay. Next, step 154 determines whether the first fixed period has timed out and, when completed, step 156 again determines whether the measured concentration level of the gas exceeds the set point in step 156. If not, possibly indicating an extraneous or false reading of the concentration level of the gas, the leak wait subroutine 114 initiates the timing of a new or third fixed period. Step 166 determines whether the presently measured gas concentration level is equal to or exceeds the set point. If yes, the subroutine 114 moves to start timing the second period and, if not, the subroutine 114 moves to step 168 to determine whether the third fixed period has timed out. If the third period has not ended, step 166 again compares the present gas concentration level with the set point. If the third period has timed out as determined in step 168, the subroutine 114 moves to step 170 to reset the leak wait counter to 0, before aborting the leak wait mode and returning to the monitoring mode and in particular to step 108.

If either step 154 or step 166 determines that the sensed gas concentration level exceeds the set point, the subroutine 114 moves to step 158 to commence the timing of the second period. In particular, step 158 decrements the leak wait counter by a value equal to the difference between the measured gas concentration level in PPM and the set point. Step 158 will decrement the leak wait counter at a fixed rate until the second, variable period time out. Thus, the length of the second period is made inversely dependent upon the measured gas concentration level. For maximum detected gas concentration levels, the second period will be relatively short, e.g., two seconds in length. For minimum measured gas concentration levels, the second period may be relatively long, e.g., greater than 3 minutes. After step 158 decrements the leak wait counter, step 160 determines whether the leak wait counter has been decremented to 0, i.e., the second variable period has timed out. If not, the leak wait subroutine 114 returns to step 156. If the sensed gas concentration level still exceeds the set point, step 158 again decrements the leak wait counter by a value equal to the difference between the sensed gas concentration level and the set point. As long as the sensed gas concentration level exceeds the set point, the leak wait counter will be decremented at a fixed rate until it reaches 0, thus ending the variable second period.

An example will illustrate how a variable second period is timed out. If the full scale value according to the maximum value of the sensed concentration level equals 255, that count or value is set into the leak wait counter. If the set point is set at 50 and a full scale value, i.e., 255, is sensed, the size of the decrement is equal to the difference 205 (255–50). Thus, if the leak wait counter is decremented at fixed intervals of 1 second, the gas monitoring apparatus 10 goes to its alarmmode at 5 seconds plus 2 seconds for the 2 decrements required to bring the leak wait counter to 0 for a total of 7 seconds. However, if a sensed concentration level is 51, the size of the decrement is equal to 1 (51–50). The gas monitoring apparatus 10 then requires 5 seconds plus 255 seconds for a total of 260 seconds to reach the alarm mode.

After the second period has timed out, the program 100 moves as shown in FIG. 5 to step 122, which enters the alarm mode and executes the alarm subroutine, whereby power is removed from the heater/anode element 24 and the collector/cathode element 26 of the gas sensor 12. As discussed above, the continued drawing of ionization current shortens the life of the sensor 12. In particular, the life of the sensor 12 is shortened as a function of the amplitude in amps of the drawn ionization current. In other words, when the gas sensor detects relatively high levels of gas concentration, the increased amperage of ionization current significantly decreases the life of the sensor 12 as compared to the detection of relatively low ionization of currents. Thus, it is important to more quickly proceed to the alarm mode when higher levels of gas concentration are detected and thereby to remove power from the sensor 12 and to prolong its life. Also, it is important in the alarm mode to more quickly throw an alarm upon sensing higher levels of gas concentration thus alerting an operator to the presence of the gas in the enclosure.

FIG. 8 shows in greater detail the steps of the alarm subroutine 122. Initially, step 186 controls the latch 78 to remove the HV and filament enable signals from the HV control circuit 68 and the PWM logic circuit 62 respectively, whereby the relatively high voltage and current are removed from elements 24 and 26 of the gas sensor 12. Next, 188 actuates the latch 78 causing the output driver 80*d* to energize the alarm light 44 and throw the alarm relay 46, whereby an alarm message is transmitted over the telephone system 48 to the central station alerting the operator there of the presence of a gas within the monitored enclosure. Next, step 190 sets the last reading of the gas concentration level into a register of the microcomputer 72, whereby that concentration level value may be displayed upon the display 42. Then, the program 100 moves to step 124, which determines whether an external reset has been made before continuing the program, i.e., whether the operator has interviewed to actuate the reset switch 73. It is necessary that an operator reset the gas monitoring apparatus 10 and to take appropriate action to cure the leak of the gas. Only after the operator has actuated the switch 13 and reset the gas monitoring apparatus 10, does the program 100 return to step 104 to continue in the monitoring mode.

Referring now to FIG. 5, the calibration mode is entered when the operator throws the run/test mode switch 82 to its test position, which is determined by step 104 before the program 100 moves to step 126. Next, the operator introduces a known concentration of the gas into the enclosure, e.g., 25 PPM. Step 126 actuates the latch 78 and the corresponding input drivers 80*a* and 80*b* to apply filament and high voltage enable signals respectively to the HV control circuit 68 and the PWM logic circuit 62, whereby the high voltage and current are applied to the elements 24 and 26 of the gas sensor 12. Next step 128 measures the ionization current drawn from the collector/cathode element 26, converting it to a digital word before comparing it with a calibration table to provide a linearized digital word indicative of the measured gas concentration level. Then step 140 converts the linearized digital word by the digital-to-analog converter 76 to an analog value, which is displayed upon display 42. The operator, while observing the display, adjusts the temperature adjust potentiometer R4, as shown in FIG. 4, until the reading on the display 42 of FIG. 3 equals precisely the known concentration of the introduced sample. The calibration mode will continue sequencing through the steps 128 and 140 until step 142 determines that the run/test mode switch 82 has been disposed to the run position, at which time the program 100 will move to the warm-up mode and in particular to step 106.

In considering this invention, it should be remembered that the present disclosure is illustrative only and that the scope of the invention should be determined by the appended claims.

I claim:

1. Apparatus for detecting the presence within a gaseous atmosphere of a gas of a concentration above a preset level, said detecting apparatus comprising:

a) a sensor including a heater/anode element and a collector/cathode element disposed to define a space therebetween through which said gaseous atmosphere flows;

b) actuable means coupled to said heater/anode element and to said collector/cathode element for applying power thereto, whereby ionization of said gas causes a current flow through said collector/cathode element of a magnitude proportional to the concentration level of said gas in said gaseous atmosphere;

c) actuable alarm means to provide an indication of the presence of the gas above the preset level; and d) control means for operating said apparatus in a monitoring mode to detect and compare said current flow with said preset level, if said current flow is equal to or exceeds said preset level, for operating said monitoring apparatus in a leak wait mode to initiate the timing of a period of variable length and, upon termination of said variable period, for operating said monitoring apparatus in an alarm mode to actuate said alarm means and to deactuate said power applying means to reduce power to said sensor and to extinguish said current flow between said heater/anode element and said collector/cathode element, said variable period having a length set inversely proportional to the magnitude of said current, whereby the life of said sensor is extended.

2. The apparatus for detecting as claimed in claim 1, wherein said length of said variable period is set inversely proportional to the difference between said detected current flow and said preset level.

3. The apparatus for detecting as claimed in claim 1, wherein said control means upon initially detecting said current flow to be equal to or greater than said preset level initiates the timing of a first fixed period.

4. The apparatus for detecting as claimed in claim 1, wherein said control means repetitively compares said detected current flow with said preset level and, if said current flow is less than said preset level, terminating said variable period.

5. The apparatus for detecting as claimed in claim 1, wherein said control means compares said detected current flow with said preset level and, if said detected current flow is equal to or exceeds said preset value, for first initiating the timing of a first fixed period.

6. The apparatus for detecting as claimed in claim 5, wherein said control means compares at the end of said first fixed period said detected current flow with said preset level and, if said then detected current flow is equal to or exceeds said preset level, for then initiating the timing of said variable period.

7. The apparatus for detecting as claimed in claim 6, wherein if said control means determines during the timing said variable period that said detected current flow is less than said preset level, said control means interrupts the timing of said variable period and initiates the timing of a further, second fixed period.

8. The apparatus for detecting as claimed in claim 1, wherein said control means operates in said leak wait mode for comparing said detected current flow with said preset level while timing said variable period and if said detected current is less than said preset level, to interrupt the timing of said variable period and to initiate the timing of a fixed period.

9. The apparatus for detecting as claimed in claim 8, wherein said control means operates during the timing of said fixed period in said leak wait mode to compare said detected current flow with said preset value and if said detected current flow is equal to or greater than said preset level, to terminate the timing of said fixed period and to continue again the timing of said variable period.

10. The apparatus for detecting as claimed in claim 9, wherein said control means operates during the timing of said fixed period in said leak wait mode and if said detected current flow remains equal to or above said preset level at the end of said variable period, for terminating said leak wait mode and then operating in said alarm mode.

11. The apparatus for detecting as claimed in claim 1, wherein said control means operates in said monitoring mode to compare said detected current flow with said preset level and if said current flow is equal to or exceeds said preset level, for first timing a first fixed period, and, if upon terminating said first fixed period said current flow is equal to or greater than said preset level, for initiating the timing of said variable period.

12. The apparatus for detecting as claimed in claim 11, wherein said control means operates in said leak wait mode to compare said current flow with said preset level while timing said first fixed period and if said current flow is less than said preset level, for terminating said leak wait mode and for resuming said monitoring mode.

13. The apparatus for detecting the presence within a gaseous atmosphere of a gas of a concentration above a preset level, said detecting apparatus comprising:
   a) means for sensing including a heater/anode element and a collector/cathode element disposed to define a space therebetween through which said gaseous atmosphere flows;
   b) actuable means coupled to said heater/anode element and to said collector/cathode element for applying power thereto, whereby ionization of said gas causes a current flow through said collector/cathode element of a magnitude proportional to the concentration level of said gas in said gaseous atmosphere;
   c) actuable alarm means to provide an indication of the presence of the gas above said preset level; and
   d) control means for operating said detecting apparatus in a monitoring mode, wherein said power applying means is actuated and said alarm means is deactuated to detect and compare said current flow with said preset level, upon first sensing current which is equal to or exceeds said preset level for operating said detecting apparatus in a leak wait mode for a period having an end thereof, in said leak wait mode said power applying means is actuated and said alarm means is deactuated to initiate the timing of said period while comparing throughout said period said detected current flow with said preset levels, and if said detected current flow remains equal to or greater than said preset level at said end of said period even though said current flow may fluctuate below said preset level during said period, for operating said detecting apparatus in an alarm mode wherein said power applying means is deactuated and said alarm means is actuated.

14. The apparatus for detecting as claimed in claim 13, wherein said control means comprises a timing counter, means upon entering said leak wait mode for loading a count in said timing counter and means for regularly decrementing said count throughout said first mentioned period and upon each decrement for comparing said detected current with said preset level.

15. The apparatus for detecting the presence within a gaseous atmosphere of a gas of a concentration above a preset level, said detecting apparatus comprising:
   a) a sensor including a heater/anode element and a collector/cathode element disposed to define a space therebetween through which said gaseous atmosphere flows:
   b) actuable means coupled to said heater/anode element and to said collector/cathode element for applying power thereto, whereby ionization of said gas causes a current flow through said collector/cathode element of a magnitude proportional to the concentration level of said gas in said gaseous atmosphere;
   c) actuable alarm means to provide an indication of the presence of the gas above said preset level; and
   d) control means for operating said detecting apparatus in a monitoring mode, wherein said power applying means is actuated and said alarm means is deactuated to detect and compare said current flow with said preset level, upon first sensing current which is equal to or exceeds said preset level for operating said detecting apparatus in a leak wait mode, wherein said power applying means is actuated and said alarm means is deactuated to initiated the timing of a period while comparing throughout said period said detected current flow with said preset level, and if said detected current flow remains equal to or greater than said preset level until said period times out, for operating said detecting apparatus in an alarm mode wherein said power applying means is deactuated and said alarm means is actuated, said control means comprising a timing counter, means upon entering said leak wait mode for loading a count in said timing counter and means for regularly decrementing said entered count throughout said first mentioned period and upon each decrement for comparing said detected current with said preset level, said decrementing means decrements with a count equal to a difference between said preset level and said detected current flow, whereby the length of said period is inversely dependent upon the magnitude of said difference.

16. The apparatus for detecting as claimed in claim 15, further comprising timing means when operating in said monitoring mode for detecting and comparing said current flow with said preset value and if equal to or greater than said preset level for initiating the timing of a first fixed period.

17. The apparatus for detecting as claimed in claim 16, wherein said timing means is responsive at the end of said first fixed period to a current flow less than said preset level for operating said detecting apparatus in said monitoring mode.

18. The apparatus for detecting as claimed in claim 17, wherein said timing means is responsive at the end of said first fixed period to said current flow greater than or equal to said preset value for initiating the timing of said variable period and to the decrementing of said leak wait counter.

19. The apparatus for detecting as claimed in claim 18, wherein said timing means is responsive during the timing of said variable period to a current less than said preset value, for interrupting the timing of said variable period and for initiating the timing of a second fixed period.

20. The apparatus for detecting as claimed in claim 19, wherein said timing means is responsive during the timing of said second fixed period to a current flow greater than or equal to said preset value to restart the timing of said variable period and said decrementing of said leak wait counter.

* * * * *